(12) United States Patent
Kim et al.

(10) Patent No.: US 9,592,496 B2
(45) Date of Patent: Mar. 14, 2017

(54) CATALYST COMPOSITION AND METHOD FOR PREPARING SAME

(71) Applicant: LG CHEM, LTD., Seoul (KR)

(72) Inventors: Dae Chul Kim, Daejeon (KR); Dong Hyun Ko, Daejeon (KR); Sung June Cho, Daejeon (KR); Jun Han Kang, Daejeon (KR); Kyong Yong Cha, Daejeon (KR); Joo Hyuck Lee, Daejeon (KR); Hyun Seok Nam, Daejeon (KR); Dae Heung Choi, Daejeon (KR); Myung Ji Suh, Daejeon (KR); Ye Seul Hwang, Daejeon (KR); Jun Kyu Han, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/763,104

(22) PCT Filed: Nov. 14, 2014

(86) PCT No.: PCT/KR2014/010955
§ 371 (c)(1),
(2) Date: Jul. 23, 2015

(87) PCT Pub. No.: WO2015/072779
PCT Pub. Date: May 21, 2015

(65) Prior Publication Data
US 2015/0352534 A1 Dec. 10, 2015

(30) Foreign Application Priority Data

Nov. 18, 2013 (KR) .................. 10-2013-0139783
Nov. 14, 2014 (KR) .................. 10-2014-0158524

(51) Int. Cl.
*B01J 23/02* (2006.01)
*B01J 23/18* (2006.01)
(Continued)

(52) U.S. Cl.
CPC .......... *B01J 27/236* (2013.01); *B01J 23/002* (2013.01); *B01J 23/007* (2013.01); *B01J 23/31* (2013.01);
(Continued)

(58) Field of Classification Search
CPC . B01J 23/007; B01J 23/02; B01J 23/18; B01J 23/28; B01J 23/31; B01J 35/1004;
(Continued)

(56) References Cited

U.S. PATENT DOCUMENTS 4,487,850 A 12/1984 Li
5,104,987 A 4/1992 King
(Continued)

FOREIGN PATENT DOCUMENTS

CN 10-3721735 * 4/2014 ............ B01J 23/745
CN 10-3785450 A * 5/2014 .............. B01J 29/46
(Continued)

OTHER PUBLICATIONS

Maurizio Bellotto et al., "Hydrotalcite Decomposition Mechanism: A Clue to the Structure and Reactivity of Spinel-like Mixed Oxides", Journal of Physical Chemistry, vol. 100, No. 20, 1996, pp. 8535-8542.
(Continued)

*Primary Examiner* — Patricia L Hailey
(74) *Attorney, Agent, or Firm* — Dentons US LLP

(57) ABSTRACT

Disclosed are a catalyst composition for oxidative dehydrogenation and a method of preparing the same. More particularly, disclosed is a catalyst composition comprising a multi-ingredient-based metal oxide catalyst and a mixed
(Continued)

metal hydroxide. The catalyst composition and the method of preparing the same according to the present disclosure may prevent loss occurring in a filling process due to superior mechanical durability and wear according to long-term use, may inhibit polymer formation and carbon deposition during reaction, and may provide a superior conversion rate and superior selectivity.

18 Claims, 2 Drawing Sheets

(51) Int. Cl.
| | |
|---|---|
| B01J 23/28 | (2006.01) |
| B01J 23/31 | (2006.01) |
| C07C 5/48 | (2006.01) |
| C07C 11/16 | (2006.01) |
| C07C 11/167 | (2006.01) |
| B01J 27/236 | (2006.01) |
| B01J 37/04 | (2006.01) |
| B01J 37/02 | (2006.01) |
| B01J 37/08 | (2006.01) |
| C01F 7/00 | (2006.01) |
| B01J 23/00 | (2006.01) |
| B01J 23/887 | (2006.01) |
| B01J 35/00 | (2006.01) |
| B01J 37/03 | (2006.01) |
| B01J 37/00 | (2006.01) |
| B01J 35/10 | (2006.01) |

(52) U.S. Cl.
CPC ......... *B01J 23/8876* (2013.01); *B01J 35/002* (2013.01); *B01J 37/0236* (2013.01); *B01J 37/04* (2013.01); *B01J 37/08* (2013.01); *C01F 7/005* (2013.01); *C07C 5/48* (2013.01); *B01J 35/1009* (2013.01); *B01J 35/1014* (2013.01); *B01J 35/1019* (2013.01); *B01J 35/1038* (2013.01); *B01J 35/1042* (2013.01); *B01J 37/0009* (2013.01); *B01J 37/0036* (2013.01); *B01J 37/03* (2013.01); *B01J 2523/00* (2013.01); *C07C 2523/28* (2013.01); *C07C 2523/31* (2013.01)

(58) Field of Classification Search
CPC B01J 35/1009; B01J 35/1014; B01J 35/1019; B01J 35/1038; B01J 35/1042; B01J 37/0009; B01J 37/02; B01J 37/0236; B01J 37/03; B01J 37/04; B01J 37/08; B01J 2231/76; C07C 5/48; C07C 11/16; C07C 11/167; C07C 2523/28; C07C 2523/31; C01F 7/005; C01P 2002/22

USPC ........ 502/300, 311; 585/624, 626, 630, 631, 585/661, 662
See application file for complete search history.

(56) References Cited

U.S. PATENT DOCUMENTS

| | | |
|---|---|---|
| 5,449,821 A | 9/1995 | Neumann et al. |
| 5,507,980 A | 4/1996 | Kelkar et al. |
| 5,922,925 A * | 7/1999 | Akporiaye ............... B01J 21/10 585/654 |
| 6,586,360 B1 | 7/2003 | Ingallina et al. |
| 7,622,623 B2 * | 11/2009 | Fridman ................. B01J 23/26 502/305 |
| 8,188,328 B2 * | 5/2012 | Fridman ................. B01J 23/26 502/106 |
| 2002/0025908 A1 * | 2/2002 | Ingallina ................. B01J 21/10 502/340 |
| 2003/0176275 A1 * | 9/2003 | Fraaije .................... C08F 10/00 502/103 |
| 2011/0172475 A1 * | 7/2011 | Peters ....................... C07C 1/24 585/254 |
| 2013/0095323 A1 * | 4/2013 | Grafov .................. B01J 35/023 428/402.24 |

FOREIGN PATENT DOCUMENTS

| | | | |
|---|---|---|---|
| EP | 1 057 530 | * 12/2000 | ............. B01J 23/22 |
| EP | 2842625 A1 | 3/2015 | |
| JP | 51-105992 | 9/1976 | |
| JP | 57-123122 A | 7/1982 | |
| JP | 09-511211 A | 11/1997 | |
| JP | 2001-009276 A | 1/2001 | |
| JP | 2011-512236 A | 4/2011 | |
| JP | 2013-538679 A | 10/2013 | |
| KR | 10-1996-0010530 A | 4/1996 | |
| KR | 1020090103424 A | 10/2009 | |
| KR | 1020110106181 A | 9/2011 | |
| KR | 1020130046214 A | 5/2013 | |
| WO | 2009044999 A1 | 4/2009 | |
| WO | 2012030891 A1 | 3/2012 | |
| WO | 2013/161702 A1 | 10/2013 | |

OTHER PUBLICATIONS

Nieto, J.M. Lopez et al.; Preparation, characterization and catalytic properties of vanadium oxides supported on calcined Mg/Al-hydrotalcite; Applied Catalysis A: General 132: 41-59 (1995).
Blasco, T. et al.; Influence of the Acid-Base Character of Supported Vanadium Catalysts on Their Catalytic Properties for the Oxidative Dehydrogenation of n-Butane; Journal of Catalysis 157: 271-282 (1995).
Nieto, J.M. Lopez et al.; Selective Oxidation of n-Butane and Butenes over Vanadium-Containing Catalysts; Journal of Catalysis 189: 147-157 (2000).

* cited by examiner

CATALYST COMPOSITION AND METHOD FOR PREPARING SAME

This application is a National Stage Application of International Application No. PCT/KR2014/010955, filed Nov. 14, 2014, and claims the benefit of Korean Application No. 10-2013-0139783, filed Nov. 18, 2013, and Korean Application No. 10-2014-0158524, filed Nov. 14, 2014, all of which are hereby incorporated by reference in their entirety for all purposes as if fully set forth herein.

TECHNICAL FIELD

The present invention relates to a catalyst composition for oxidative dehydrogenation and a method of preparing the same. More particularly, the present invention relates to a catalyst composition for oxidative dehydrogenation to prevent loss occurring in a filling process due to superior mechanical durability and wear according to long-term use, to inhibit polymer formation and carbon deposition during reaction and to provide a superior conversion rate and superior selectivity, and a method of preparing the same.

BACKGROUND ART

Butene oxidative dehydrogenation as a representative method of preparing butadiene as a raw material of synthetic rubber is carried out at 300 to 450° C. In this regard, oxygen, water, etc. as an oxidizing agent are added thereto, but butadiene is prepared only using butane. However, a metal oxide catalyst such as molybdenum, bismuth or cobalt as a catalyst for oxidative dehydrogenation of butane is prepared into a pellet through preparation and molding processes, and, when a reactor is filled with these catalysts, some thereof is lost. In addition, due to use of the catalysts, wear occurs. In particular, during molding a metal oxide precursor and then firing the same, various problems such as fragmentation of a pellet occur.

Accordingly, there is an urgent need for a catalyst composition for oxidative dehydrogenation of butane in order to minimize catalyst loss occurring upon filling a reactor with a catalyst and catalyst wear according to use, and a method of preparing the same.

DISCLOSURE

Technical Problem

Therefore, the present invention has been made in view of the above problems, and it is one object of the present invention to provide a catalyst composition to prevent loss occurring in a filling process due to superior mechanical durability and wear according to long-term use, to inhibit polymer formation and carbon deposition during reaction and to provide a superior conversion rate and superior selectivity, a method of preparing the same, and a binder applied thereto.

The above and other objects can be accomplished by the present invention described below.

Technical Solution

In accordance with one aspect of the present invention, provided is a catalyst composition comprising a multi-ingredient-based metal oxide catalyst and a mixed metal hydroxide.

In accordance with another aspect of the present invention, provided is a method of preparing a catalyst composition, the method comprising a) mixing a multi-ingredient-based metal oxide catalyst and a mixed metal hydroxide, b) molding the mixture, and c) firing the molded material.

In accordance with yet another aspect of the present invention, provided is a binder that is a mixed metal hydroxide and applied to a multi-ingredient-based metal oxide catalyst.

Advantageous Effects

As apparent from the fore-going, the present invention advantageously provides a catalyst composition to prevent loss occurring in a filling process due to superior mechanical durability and wear according to long-term use, to inhibit polymer formation and carbon deposition during reaction and to provide a superior conversion rate and superior selectivity, and a method of preparing the same.

BEST MODE

Figure 1:
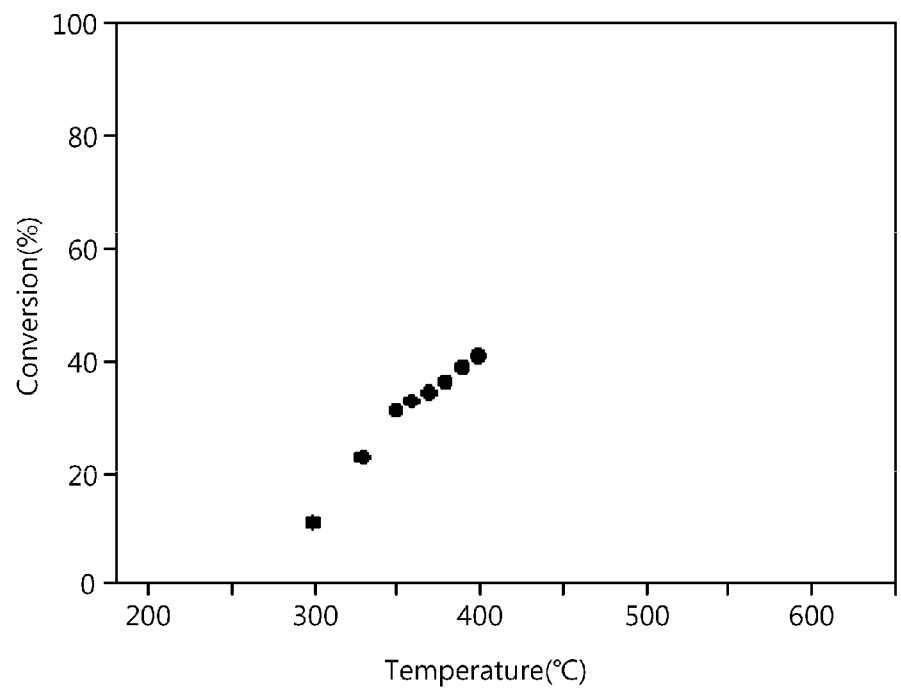
FIG. 1 is a graph illustrating an oxidative dehydrogenation conversion rate of butene according to reaction temperature of a catalyst composition pellet prepared according to Example 1 (based on 1-butene 5 cc, oxygen 12 cc and helium 84 cc per minute)

Hereinafter, the present invention is described in detail.

A catalyst composition according to the present disclosure comprises a multi-ingredient-based metal oxide catalyst and a mixed metal hydroxide.

In an embodiment, the multi-ingredient-based metal oxide catalyst may comprise bismuth and molybdenum. In this case, superior conversion rate and selectivity are exhibited.

In another embodiment, the multi-ingredient-based metal oxide catalyst may comprise bismuth, molybdenum and cobalt. In this case, superior conversion rate and selectivity are exhibited.

In an embodiment, the multi-ingredient-based metal oxide catalyst may be a catalyst for oxidative dehydration reaction.

In an embodiment, the multi-ingredient-based metal oxide catalyst may be a coprecipitation catalyst. In this case, strength of the metal oxide catalyst is enhanced, and a structure of the catalyst is maintained. Accordingly, in addition, superior activity and selectivity are exhibited.

In an embodiment, a specific surface area of the multi-ingredient-based metal oxide catalyst is 2 to 15 $m^2 \, g^{-1}$, 3 to 12 m² g⁻¹ or 5 to 10 m² g⁻¹. Within these ranges, the catalyst exhibits superior activity and selectivity.

In an embodiment, the multi-ingredient-based metal oxide catalyst has a pore volume of 0.01 to 0.1 ccg⁻¹, 0.01 to 0.06 ccg⁻¹ or 0.02 to 0.05 ccg⁻¹. Within these ranges, the catalyst exhibits superior activity and selectivity.

In an embodiment, in the oxidative dehydration reaction, butadiene is generated from butane or butene.

In an embodiment, the mixed metal hydroxide is a plate structure or a layered structure. In this case, a wider specific surface area than conventional metal hydroxide is possible.

The plate structure or the layered structure according to the present disclosure is not specifically limited. In an embodiment, thickness may be larger than a side length. In another embodiment, a value of a side length to thickness (L/T) may be 1.5 to 5.

In an embodiment, the specific surface area of the mixed metal hydroxide may be 5 to 500 m² g⁻¹, 10 to 300 m² g⁻¹ or 50 to 200 m² g⁻¹. Within these ranges, binding of the metal hydroxide to the catalyst is increased.

In an embodiment, a pore volume of the mixed metal hydroxide may be 0.1 to 1.0 ccg⁻¹, 0.1 to 0.5 ccg⁻¹ or 0.2 to 0.5 ccg⁻¹. Within these ranges, binding of the metal hydroxide to the catalyst is increased.

In an embodiment, the mixed metal hydroxide comprises aluminum and magnesium. In this case, the metal oxide catalyst exhibits enhanced strength.

In an embodiment, a molar ratio of aluminum to magnesium is 1:6 to 6:1, 1:1 to 6:1, or 2:1 to 4:1. Within these ranges, the metal oxide catalyst exhibits superior strength.

In another embodiment, the mixed metal hydroxide is hydrotalcite. In this case, the metal oxide catalyst exhibits superior strength.

In an embodiment, the amount of the mixed metal hydroxide is 0.01 to 20% by weight, 0.1 to 5% by weight, or 1 to 2.5% by weight based on 100% by weight of the catalyst composition. Within these ranges, superior crush strength, butene conversion rate and butadiene selectivity are exhibited.

The weight of the catalyst composition according to the present disclosure means the weight of a mixture of the multi-ingredient-based metal oxide and the mixed metal hydroxide, or the weight of the fired catalyst composition.

In an embodiment, the catalyst composition may be fired. In this case, an amorphous metal oxide catalyst exhibits enhanced strength.

In an embodiment, the catalyst composition is a coprecipitation catalyst. In this case, strength of the metal oxide catalyst is increased and a structure of the catalyst is maintained. Accordingly, superior activity and selectivity are exhibited.

In an embodiment, the catalyst composition is a pellet type. In this case, strength of the metal oxide catalyst is enhanced.

In an embodiment, the catalyst composition may have a crush strength (Newton) of 4.5 or more, 4.5 to 15 or 7 to 14. Within these ranges, molding may be carried out into a variety of morphologies, and superior activity and selectivity are exhibited.

In an embodiment, a specific surface area of the catalyst composition is 5 to 500 m² g⁻¹, 10 to 300 m² g⁻¹ or 50 to 250 m² g⁻¹. Within these ranges, strength of the metal oxide catalyst is enhanced.

In an embodiment, a pore volume of the catalyst composition may be 0.01 to 0.5 ccg⁻¹, 0.01 to 0.3 ccg⁻¹ or 0.02 to 0.3 ccg⁻¹. Within these ranges, the strength of the metal oxide catalyst is enhanced.

A method of preparing a catalyst composition according to the present disclosure comprises a) mixing a multi-ingredient-based metal oxide catalyst and a mixed metal hydroxide, b) molding the mixture, and c) firing the molded material.

In an embodiment, the method of preparing the catalyst composition may comprise a) preparing a slurry by mixing the multi-ingredient-based metal oxide catalyst, the mixed metal hydroxide and water, b) preparing a molded material by molding the slurry and c) firing the molded material. In this case, strength of the metal oxide catalyst is enhanced, and, when compared with conventional metal oxide catalysts, superior conversion rate and selectivity are exhibited upon butadiene generation.

Since, in the method of preparing the catalyst composition according to the present disclosure, heat-treating among conventional processes of preparing, molding and heat-treating a multi-ingredient-based metal oxide is omitted, process simplification may be accomplished and production costs may be reduced.

The fired catalyst composition shows similar reactivity when compared with a multi-ingredient-based metal oxide catalyst powder in oxidative dehydration reactivity (conversion rate and selectivity) of butene.

In an embodiment, in the mixing (a), the multi-ingredient-based metal oxide catalyst may be prepared through i) coprecipitating, ii) drying and iii) firing. In this case, strength of the metal oxide catalyst is enhanced.

In an embodiment, in the mixing (a), the mixed metal hydroxide is fired at 500 to 600° C., 550 to 600° C. or 570 to 580° C. Within these ranges, self-adhesion is superior and thus strength of the catalyst is enhanced.

In an embodiment, in the mixing (a), water is mixed in an amount of 50 to 100 parts by weight, 10 to 20 parts by weight or 5 to 7 parts by weight based on 100 parts by weight of a mixture of the multi-ingredient-based metal oxide catalyst and the mixed metal hydroxide. Within these ranges, a pellet may be easily molded and strength of the metal oxide catalyst is enhanced.

In an embodiment, the water may be double-distilled water at 5° C. or less, 0° C. or less, or 5 to −10° C. In this case, time required in mixing and molding processes may be secured by decreasing a reaction rate.

In an embodiment, the amount of the mixed metal hydroxide may be 0.01 to 20% by weight, 0.1 to 5% by weight, or 1 to 2.5% by weight based on the total weight of a mixture of the multi-ingredient-based metal oxide and the mixed metal hydroxide. Within these ranges, excellent crush strength, butene conversion rate and butadiene selectivity are exhibited.

In an embodiment, the molded material of the molding (b) is a pellet type. In this case, the size of the catalyst composition may be easily controlled.

In an embodiment, the firing (c) may be carried out at 200 to 500° C., 300 to 400° C. or 300 to 350° C. Within these ranges, excellent crush strength, butene conversion rate and butadiene selectivity are exhibited.

In an embodiment, the firing (c) may be carried out for 1 to 8 hours, 2 to 6 hours, or 3 to 4 hours. Within these ranges, excellent crush strength is exhibited.

In an embodiment, the method of preparing the catalyst composition may further comprise aging the molded material before the firing (c). In this case, excellent crush strength is exhibited.

In an embodiment, the aging may be carried out at room temperature or at 20 to 30° C. for 12 to 96 hours or 20 to 30 hours. Within these ranges, excellent crush strength is exhibited.

A method of the aging is not specifically limited so long as the method is conventionally used in the art.

In an embodiment, the method of preparing the catalyst composition may further comprise drying the molded material before c) the firing.

In an embodiment, the drying may be carried out at room temperature or at 20 to 30° C. for 12 to 96 hours or 10 to 15 hours. Within these ranges, excellent crush strength is exhibited.

The binder according to the present disclosure is a mixed metal hydroxide and is applied to the multi-ingredient-based metal oxide catalyst.

In an embodiment, the mixed metal hydroxide comprises aluminum and magnesium. In this case, excellent crush strength, butene conversion rate and butadiene selectivity are exhibited.

In another embodiment, the mixed metal hydroxide is hydrotalcite. In this case, excellent crush strength, butene conversion rate and butadiene selectivity are exhibited.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

EXAMPLE

Example 1

A coprecipitation-fired a molybdenum-bismuth-iron-cobalt ($Mo_{12}Bi_1Fe_1Co_8$) composite oxide catalyst having a specific surface area of 5 $M^2\ g^{-1}$ and a pore volume of 0.03 $ccg^{-1}$ was ground into a fine powder at room temperature using a ball mill, and then, hydrotalcite having a plate structure was added thereto in an amount of 1.25% by weight, followed by mixing. Thereto, double-distilled water maintained at 0° C. was added in an amount of 50 parts by weight based on 100 parts by weight of the mixed powder and mixed, thereby preparing a slurry. The slurry was injection-molded under a pressure of 80-100 $kgcm^{-2}$, thereby preparing a globular pellet. The prepared pellet was aged at room temperature for 24 hours and then dried for 24 hours. In order to enhance strength, the dried pellet was fired (heat-treated) at 300° C. for two hours, thereby preparing a final catalyst composition.

Example 2

A catalyst composition was prepared in the same manner as in Example 1, except that the hydrotalcite was added in an amount of 1.3% by weight based on 100% by weight of the mixed powder.

Example 3

A catalyst composition was prepared in the same manner as in Example 1, except that the hydrotalcite was added in an amount of 1.3% by weight based on 100% by weight of the mixed powder and firing was carried out at 350° C.

Example 4

A catalyst composition was prepared in the same manner as in Example 1, except that the hydrotalcite was added in an amount of 2.5% by weight based on 100% by weight of the mixed powder.

Example 5

A catalyst composition was prepared in the same manner as in Example 1, except that the hydrotalcite was added in an amount of 2.5% by weight based on 100% by weight of the mixed powder and firing was carried at 350° C.

Example 6

A catalyst composition was prepared in the same manner as in Example 1, except that the hydrotalcite was added in an amount of 3.0% by weight based on 100% by weight of the mixed powder.

Example 7

A catalyst composition was prepared in the same manner as in Example 1, except that the hydrotalcite was added in an amount of 3.0% by weight based on 100% by weight of the mixed powder and firing was carried out at 350° C.

Comparative Example 1

A catalyst composition was prepared in the same manner as in Example 1, except that silica instead of the hydrotalcite was added in an amount of 2.0% by weight based on 100% by weight of the mixed powder.

Comparative Example 2

A catalyst composition was prepared in the same manner as in Example 1, except that alumina instead of hydrotalcite was added in an amount of 1.25% by weight based on 100% by weight of the mixed powder.

Comparative Example 3

A catalyst composition was prepared in the same manner as in Example 1, except that the hydrotalcite was not added.

Comparative Example 4

A catalyst composition was prepared in the same manner as in Example 1, except that the hydrotalcite was not added and the firing was carried out at 350° C.

Comparative Example 5

A catalyst composition was prepared in the same manner as in Example 1, except that aluminum hydroxide instead of the hydrotalcite was added in an amount of 1.25% by weight based on 100% by weight of the mixed powder.

Test Example

Each of the prepared catalyst compositions was reacted at a reaction temperature of 380° C. using a fixed-bed reactor such that a reaction product had a composition ratio of 1-butene:oxygen:helium of 5:12:84. Subsequently, a composition, etc. of generated butadiene was analyzed using gas chromatography (GC).

Properties of the catalyst compositions prepared according to Examples and Comparative Examples were measured according to methods below, and results are summarized in Tables 1 and 2 below.

Crush strength (Newton): Measured using a multifunctional tensile strength test machine.
Carbon deposition: Measured according to a TGA method.
Conversion rate: Measured according to a GC method.
Selectivity: Measured according to a GC method.
Yield: Measured according to a GC method.
Specific surface area: Measured according to a BET method.
Pore volume: Measured according to a BET method.

TABLE 1

| Classification | Mixed metal oxide | | | Catalyst composition | | | |
|---|---|---|---|---|---|---|---|
| | Shape | Specific surface area | Pore volume | Crush strength | Conversion rate | Selectivity | Yield |
| Example 1 | Plate structure | 3 | 0.01 | 4.51 | 45 | 95 | 43 |
| Example 2 | Plate structure | 5 | 0.02 | 7.75 | 44 | 92 | 40 |
| Example 3 | Plate structure | 5 | 0.02 | 9.71 | 45 | 95 | 43 |
| Example 4 | Plate structure | 7 | 0.03 | 10.44 | 44 | 96 | 42 |
| Example 5 | Plate structure | 7 | 0.03 | 13.64 | 51 | 94 | 48 |
| Example 6 | Plate structure | 10 | 0.05 | 13.81 | 24 | 92 | 22 |
| Example 7 | Plate structure | 10 | 0.05 | 12.95 | 19 | 92 | 17 |
| Comparative Example 1 | Amorphous | 3 | 0.01 | 4.10 | 44 | 93 | 41 |
| Comparative Example 2 | Amorphous | 5 | 0.02 | 9.51 | 20 | 60 | 12 |
| Comparative Example 3 | Amorphous | 3 | 0.01 | 4.36 | 45 | 95 | 43 |
| Comparative Example 4 | Amorphous | 3 | 0.01 | 6.10 | 35 | 75 | 26 |
| Comparative Example 5 | Amorphous | 8 | 0.05 | 5.10 | 20 | 60 | 12 |

As shown in Table 1, it can be confirmed that the catalyst composition according to the present disclosure exhibits excellent crush strength, conversion rate and selectivity, etc., when compared with the catalyst compositions (Comparative Examples 1 to 5) which do not comprise the mixed metal hydroxide.

In addition, it can be confirmed that a crystal structure of the catalyst is maintained since the catalyst composition according to the present disclosure binds to the multi-ingredient-based metal oxide catalyst in which the mixed metal hydroxide is fired, crush strength of the pellet may be easily controlled since a use amount of the mixed metal hydroxide is not specifically limited, catalyst activity reduction due to an increased addition amount of the mixed metal hydroxide may be controlled by changing the composition of the catalyst, crush strength is only increased without catalyst activity change up to 2.5% by weight of the mixed metal hydroxide, and subsidiary effects such as side-reaction decrease due to basic properties of the mixed metal hydroxide are exhibited.

However, in the case in which a binder is added to a multi-ingredient-based metal oxide catalyst before firing, deformation of a coprecipitated structure is caused, and it is difficult to mold a fired a multi-ingredient-based metal oxide catalyst with water or a silica sol-based binder. In addition, when, in order to minimize deformation of a coprecipitated structure, only water or a small amount of binder is added as a binder, crush strength of a prepared pellet is decreased.

Figure 2:
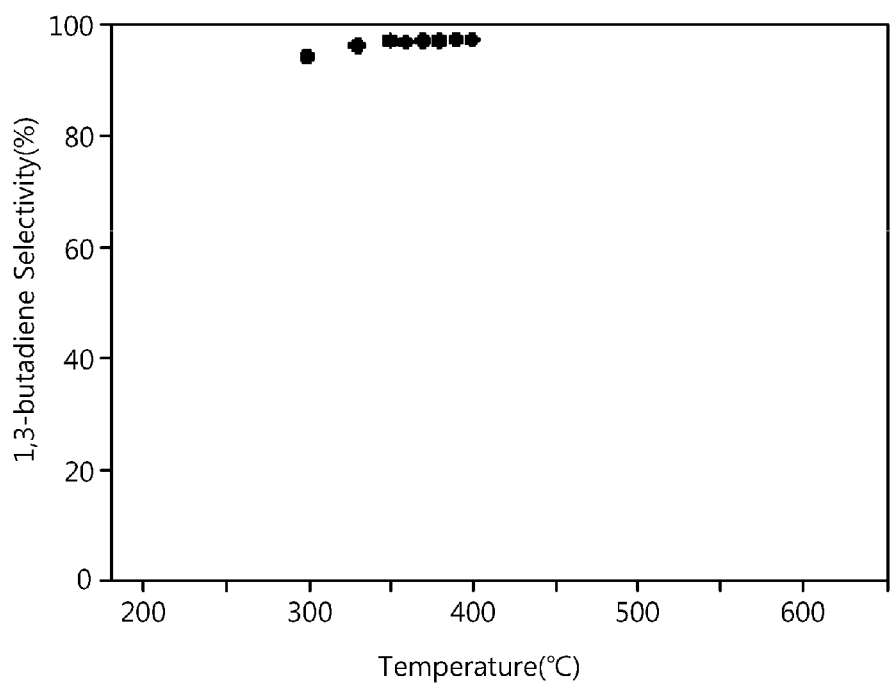
FIG. 2 is a graph illustrating 1,3-butadiene selectivity (1-butene 5 cc, oxygen 12 cc and helium 84 cc per minute) in oxidative dehydrogenation of butane according to reaction temperature of a catalyst composition pellet prepared according to Example 1.

Next, as illustrated in FIGS. 1 and 2, it can be confirmed that the catalyst composition prepared according to Example 1 exhibits that butene oxidated dehydration reaction conversion rate according to reaction temperature is constant and a 1,3-butadiene selectivity of 90% or more in butene oxidated dehydration reaction according to reaction temperature is maintained.

Figure 3:
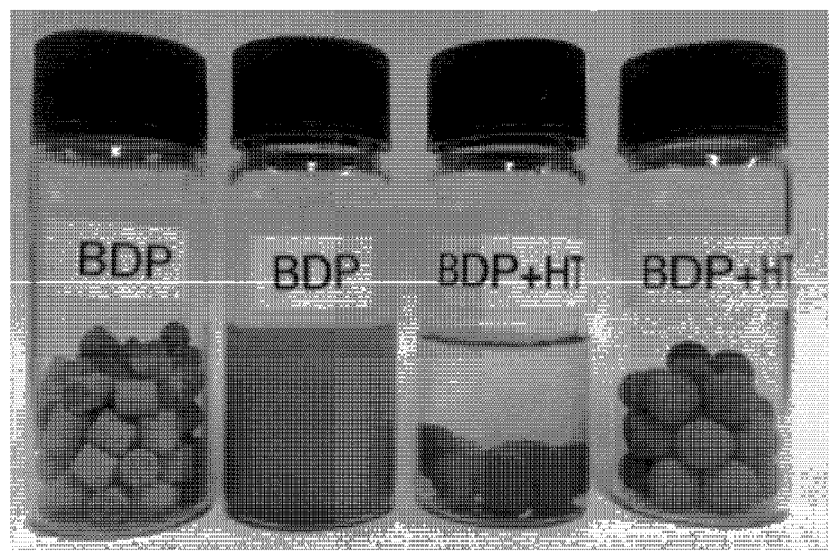
FIG. 3 is a graph illustrating states of a catalyst composition (BDP+HT) comprising a mixed metal hydroxide and a catalyst composition (BDP) not comprising the mixed metal hydroxide before and after soaking in water, respectively.

In addition, as illustrated in FIG. 3 below, it can be confirmed that the catalyst composition according to the present disclosure (Examples 3 and 4) maintains a shape thereof in water as it is due to high crush strength but the catalyst composition (Comparative Example 3) not comprising the mixed metal hydroxide is softened and crushed in water due to low crush strength thereof, there leading to cloudy water.

TABLE 2

| Classification | HT content | Firing temperature | Crush strength | |
|---|---|---|---|---|
| | | | Horiz. | Vert. |
| Example 2 | 1.3% by weight | 300° C. | 7.75 | 6.26 |
| Example 3 | 1.3% by weight | 350° C. | 9.71 | 7.45 |
| Example 4 | 2.5% by weight | 300° C. | 10.44 | 8.45 |
| Example 5 | 2.5% by weight | 350° C. | 13.64 | 11.29 |
| Example 6 | 3.0% by weight | 300° C. | 13.81 | 8.34 |
| Example 7 | 3.0% by weight | 350° C. | 12.95 | 11.40 |
| Comparative Example 3 | 0.0% by weight | 300° C. | 4.36 | 4.83 |
| Comparative Example 4 | 0.0% by weight | 350° C. | 4.87 | 3.68 |

Figure 4:
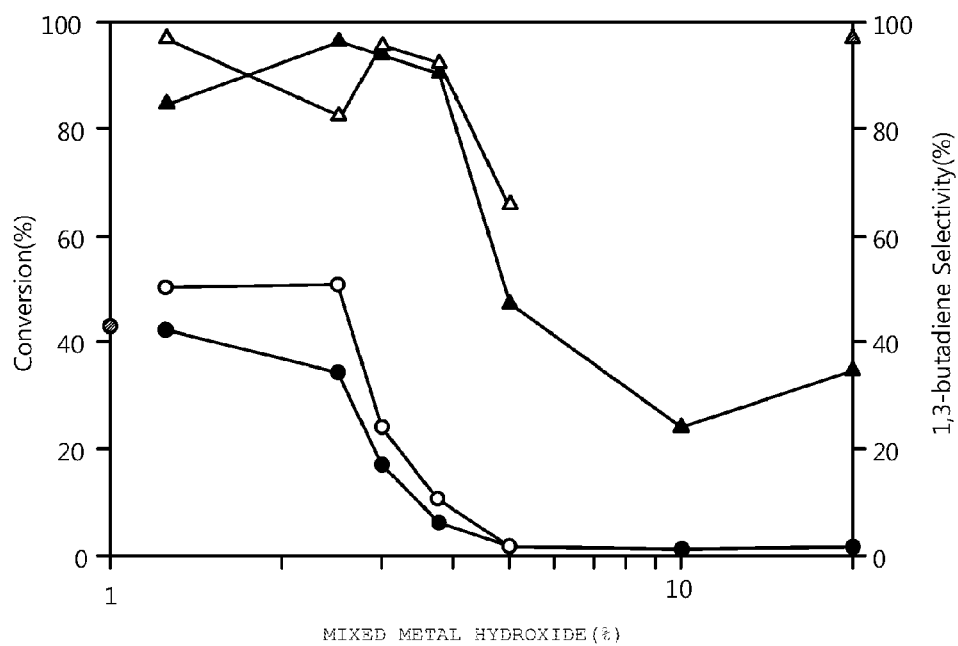
FIG. 4 is a graph illustrating an oxidative dehydrogenation conversion rate of butene and 1,3-butadiene selectivity (with respect to a reaction temperature of 380° C., and 1-butene 5 cc, oxygen 12 cc and helium 84 cc per minute) according to content change of a mixed metal hydroxide in a catalyst composition according to the present disclosure.

As shown in Table 2 and FIG. 4 below, it can be confirmed that, in the catalyst compositions according to the present disclosure, crush strength is only increased without catalyst activity change up to 2.5% by weight of the mixed metal hydroxide, and catalyst activity is decreased with increase of crush strength from 3.0% by weight of the mixed metal hydroxide (in FIG. 4, ●: butene conversion rate in 300° C. reaction, ▲: 1,3-butadiene selectivity in 300° C. reaction, ○: butene conversion rate in 350° C. reaction, Δ: 1,3-butadiene selectivity in 350° C. reaction, ◉: butene conversion rate in catalyst composition not comprising mixed metal hydroxide, and △: 1,3-butadiene conversion rate in catalyst composition not comprising mixed metal hydroxide).

What is claimed is:

1. A catalyst composition comprising a multi-ingredient-based metal oxide catalyst and a mixed metal hydroxide,
wherein the multi-ingredient-based metal oxide catalyst comprises bismuth and molybdenum.

2. The catalyst composition according to claim 1, wherein the multi-ingredient-based metal oxide catalyst is a catalyst for oxidative dehydration reaction.

3. The catalyst composition according to claim 2, wherein the oxidative dehydration reaction is a reaction generating butadiene from butane or butene.

4. The catalyst composition according to claim 1, wherein the mixed metal hydroxide has a plate structure or a layered structure.

5. The catalyst composition according to claim 1, wherein the mixed metal hydroxide has a specific surface area of 5 to 500 $m^2g^{-1}$.

6. The catalyst composition according to claim 1, wherein a pore volume of the mixed metal hydroxide is 0.1 to 1.0 $ccg^{-1}$.

7. The catalyst composition according to claim 4, wherein the mixed metal hydroxide comprises aluminum and magnesium.

8. The catalyst composition according to claim 4, wherein the mixed metal hydroxide is hydrotalcite.

9. The catalyst composition according to claim 1, wherein a content of the mixed metal hydroxide is 0.01 to 20% by weight.

10. The catalyst composition according to claim 1, wherein the catalyst composition has a crush strength (Newton) of 4.5 or more.

11. A method of preparing a catalyst composition, the method comprising a) mixing a multi-ingredient-based metal oxide catalyst and a mixed metal hydroxide, b) molding the mixture, and c) firing the molded material,
wherein the multi-ingredient-based metal oxide catalyst comprises bismuth and molybdenum.

12. The method according to claim 11, wherein a) the multi-ingredient-based metal oxide catalyst is prepared through i) coprecipitating, ii) drying and iii) firing.

13. The method according to claim 11, wherein the a) the mixed metal hydroxide is fired at 500 to 600° C.

14. The method according to claim 11, wherein the a) in the mixing, 50 to 100 parts by weight of water is mixed with 100 parts by weight of a mixture of the multi-ingredient-based metal oxide catalyst and the mixed metal hydroxide.

15. The method according to claim 11, wherein the c) the firing is carried out at 200 to 500° C.

16. The method according to claim 11, further comprising aging the molded material before c) the firing.

17. The method according to claim 16, further comprising drying the molded material before c) the firing.

18. A binder, wherein the binder is a mixed metal hydroxide and is applied to a multi-ingredient-based metal oxide catalyst, wherein the multi-ingredient-based metal oxide catalyst comprises bismuth and molybdenum.

* * * * *